United States Patent
Hanbury

(10) Patent No.: US 10,328,236 B2
(45) Date of Patent: Jun. 25, 2019

(54) METHODS AND SYSTEMS FOR PROVIDING STIMULI TO THE BRAIN

(71) Applicant: Sana Health, Inc., San Rafael, CA (US)

(72) Inventor: Richard Hanbury, San Rafael, CA (US)

(73) Assignee: SANA HEALTH, INC., San Rafael, CA (US)

( * ) Notice: Subject to any disclaimer, the term of this patent is extended or adjusted under 35 U.S.C. 154(b) by 88 days.

(21) Appl. No.: 15/360,808

(22) Filed: Nov. 23, 2016

(65) Prior Publication Data

US 2017/0143935 A1 May 25, 2017

Related U.S. Application Data

(60) Provisional application No. 62/258,965, filed on Nov. 23, 2015.

(51) Int. Cl.
*A61M 21/02* (2006.01)
*A61M 21/00* (2006.01)

(52) U.S. Cl.
CPC ....... *A61M 21/02* (2013.01); *A61M 2021/005* (2013.01); *A61M 2021/0022* (2013.01); *A61M 2021/0027* (2013.01); *A61M 2205/3569* (2013.01); *A61M 2205/3592* (2013.01); *A61M 2205/505* (2013.01); *A61M 2209/088* (2013.01)

(58) Field of Classification Search
CPC ................. A61M 21/00; A61M 21/02; A61M 2021/0005; A61M 2021/0022; A61M 2021/0027; A61M 2021/0044
See application file for complete search history.

(56) References Cited

U.S. PATENT DOCUMENTS

| 4,315,502 A | * | 2/1982 | Gorges | ................... A61B 5/486 434/236 |
| 4,892,106 A | * | 1/1990 | Gleeson, III | .......... A61M 21/00 600/27 |
| 5,343,261 A | | 8/1994 | Wilson | |
| 8,562,659 B2 | * | 10/2013 | Wells | ................... A61B 5/6821 607/88 |
| 8,838,247 B2 | | 9/2014 | Hagedorn et al. | |
| 2010/0323335 A1 | * | 12/2010 | Lee | .......................... A61B 5/16 434/236 |
| 2011/0075853 A1 | | 3/2011 | Anderson | |

(Continued)

OTHER PUBLICATIONS

PCT Search Report & Written Opinion, PCT/US2016063651.
PCT Search Report & Written Opinion, PCT/US2018/020547.

*Primary Examiner* — Carrie R Dorna
(74) *Attorney, Agent, or Firm* — Dickinson Wright PLLC

(57) ABSTRACT

Visual and auditory stimuli are provided to a patient to treat various neurological disorders or conditions and/or to provide improved mental or physical performance. The visual and auditory stimuli are provided by a wearable headset or sleep mask that may be comfortably worn by a user, such as in bed to induce sleep. The wearable headset or sleep mask is operated by a personal computing device of the user, such as smartphone, having downloaded and active thereon a control application or app for the therapy. The wearable headset or sleep mask also concurrently provides tactile stimuli, and the tactile stimulus is provided from bone conduction transducers that concurrently provides the auditory stimuli.

30 Claims, 6 Drawing Sheets

(56) References Cited

U.S. PATENT DOCUMENTS

| | | |
|---|---|---|
| 2011/0213664 A1 | 9/2011 | Osterhout |
| 2012/0095534 A1* | 4/2012 | Schlangen ............ A61M 21/00 607/90 |
| 2012/0211013 A1* | 8/2012 | Otis .................... A61N 5/0618 128/898 |
| 2013/0267759 A1 | 10/2013 | Jin |
| 2014/0336473 A1 | 11/2014 | Greco |
| 2015/0268673 A1 | 9/2015 | Farzbod et al. |

* cited by examiner

METHODS AND SYSTEMS FOR PROVIDING STIMULI TO THE BRAIN

CROSS-REFERENCE

This application claims the benefit of U.S. Provisional Application No. 62/258,965, filed Nov. 23, 2015, the contents of which are hereby incorporated by reference in its entirety.

BACKGROUND OF THE INVENTION

Field of the Invention

The present disclosure relates to medical devices and methods. In particular, the present disclosure relates to providing stimuli to a subject to treat various neurological disorders or conditions and/or to provide performance enhancement.

Discussion of the Background

Sensory stimulation has been applied to treat various disorders. For example, binaural beats have applied to induce various mental states to encourage sleep, relaxation, meditation, creativity, and other desirable mental states. Combinations of auditory and visual stimuli have been applied to encourage such mental states as well. The application of such therapy, however, has been less than ideal in many circumstances. Equipment to provide the stimulus can be bulky, expensive, generally inaccessible, and below the critical efficacy threshold for widespread use, typically only helping subsets of the population. Users may find the use of such equipment difficult in many circumstances, such as when trying to sleep in a bedroom or an airplane cabin.

To treat various neurological disorders and conditions, pharmaceuticals and/or supplements are often used instead of sensory stimulation. The use of pharmaceuticals, however, can be less than ideal in many circumstances. Often, pharmaceuticals are expensive, rely on patient-compliance, and may require a prescription from a medical professional. Pharmaceuticals may be effective in only a small, less than ideal portion of the general population. To treat insomnia, for example, pharmaceuticals and supplements such as melatonin and zolpidem (e.g., AMBIEN™) have questionable efficacy. Pharmaceuticals often lead to undesirable side effects. For example, some pharmaceutical for treating insomnia can lead to deprivation in certain ranges of deep sleep and increases in mortality rates.

For at least these reasons, improved methods and systems to treat neurological disorders and other conditions that overcome at least some of the aforementioned challenges are desired.

BRIEF SUMMARY OF THE INVENTION

The present disclosure relates to medical devices and methods which may be used, for example, to provide stimulus to a subject to treat various neurological disorders or conditions, where the stimulus provided may include one or more of an auditory, a visual, or a tactile stimulus. Examples of neurological disorders which may be treated with devices and methods may include, but are not limited to, insomnia, post-traumatic stress disorder (PTSD), brain injuries including, but not limited to traumatic brain injury (TBI), mild traumatic brain injury (mTBI), or injury from oxygen deprivation of the brain from strokes, depression, anxiety, mood disorders, personality disorders, eating disorders, psychotic disorders, and balance disorders, to name a few. Alternatively or in combination, the stimulus provided by the medical devices and methods described herein may provide cognitive benefits and/or enhancement, including, but not limited to, improving neuroplasticity, motor skills, coordination, reaction times, alertness, energy, working memory, mood, and feelings of wellbeing.

In certain embodiments, stimuli may be provided to the wearer of a headset or sleep mask that may be comfortably worn by a user, such as in bed to induce sleep. The wearable headset or sleep mask may be operated by a personal computing device of the user, such as smartphone, having downloaded and active thereon a control application or "app" for the therapy. The wearable headset or sleep mask may also concurrently provide tactile stimuli, and the tactile stimuli may be provided from bone conduction transducer that may concurrently provide the auditory stimuli. Various patterns of the stimuli to induce different user responses are also disclosed.

In certain embodiments, a device is provided that produces an output that may be perceived by a user of the device as a visual, auditory or tactile stimuli at one or more frequencies, or in one or more frequency ranges. In certain embodiments, the stimuli may be turned on and off at frequencies that are believed to induce one or more frequencies of electrical activity in the brain, which are generally accepted as being delta waves (1.0 to 3.0 Hz), theta waves (3.0 to 7.0 Hz), alpha waves (7.0 to 12 Hz), beta waves (12 to 38 Hz), and gamma waves (38 to 42 Hz).

Thus, for example, one embodiment device produces an output that may be perceived by a user of the device as a stimuli at sequential frequencies, such as sequences of alpha waves, theta waves, and delta waves. In certain embodiments, the stimuli is a coordinated auditory and visual stimulation, providing right and left eyes and ears to pulsed light and pulsed auditory in each of the ranges listed above. As one example, the coordinated stimulation may be: 1) both eyes and both ears being stimulated at the same time; 2) the left eye and ear being stimulated at the same time, followed by the right eye and ear being stimulated at the same time; 3) both eyes being stimulated at the same time, followed by both ears being stimulated at the same time; or 4) the right eye and left ear being stimulated at the same time, followed by the left eye and right eye being stimulated at the same time. In each case, the stimulation may include, for example, sequentially stimulating in the alpha wave range, followed by the theta wave range, followed by the delta wave range. The stimulation can last for a period of one minute up to an hour.

It is one aspect to provide a method to provide stimulation to a user. The method includes: providing a headset to be worn by the user; applying, with the headset, a left visual stimulus pattern to the left eye of the user; applying, with the headset, a right visual stimulus pattern to the right eye of the user; applying, with the headset, a left auditory stimulus pattern to the left side of a head of the user; and applying, with the headset, a right auditory stimulus pattern to the right side of the head. The applications of the left visual stimulus pattern, the right visual stimulus pattern, the left auditory stimulus pattern, and the right auditory stimulus pattern are coordinated with one another.

It is another aspect to provide a method of treating a neurological disease or condition or providing performance enhancement using the method of providing stimulation to a user. The method includes: providing a headset to be worn by the user; applying, with the headset, a left visual stimulus pattern to the left eye of the user; applying, with the headset, a right visual stimulus pattern to the right eye of the user; applying, with the headset, a left auditory stimulus pattern to the left side of a head of the user; and applying, with the headset, a right auditory stimulus pattern to the right side of the head. The applications of the left visual stimulus pattern, the right visual stimulus pattern, the left auditory stimulus pattern, and the right auditory stimulus pattern are coordinated with one another.

It is one aspect to provide an apparatus to provide stimulation to a user. The apparatus includes: a frame configured to be worn on a head of a user; a left light source configured to generate a left visual stimulus pattern; a right light source configured to generate a right visual stimulus pattern; a left auditory source configured to generate a left auditory stimulus pattern; a right auditory source configured to generate a right auditory stimulus pattern; and a controller coupled to the left light source, the right light source, the left auditory source, and the right auditory source, The applications of the left visual stimulus pattern, the right visual stimulus pattern, the left auditory stimulus pattern, and the right auditory stimulus pattern are independently controlled from one another but coordinated with one another by the controller.

It is yet another aspect to provide a method to provide stimulation to a user, the method includes: concurrently providing a left-side light stimulus to a left eye of the user, a right-side light stimulus to a right eye of the user, a left-side auditory stimulus to a left side of the user, and a right-side auditory stimulus to a right side of the user for a first time interval; alternating providing the left-side light stimulus and left-side auditory stimulus with providing the right-side light stimulus and right-side auditory stimulus for a second time interval; alternating providing the left-side and right-side light stimuli with providing the left-side and right-side auditory stimuli for a third time interval; and alternating providing the left-side light stimulus and right-side auditory stimulus with providing the right-side light stimulus and left-side auditory stimulus for a fourth time interval.

It is one aspect to provide a method of treating a neurological disease or condition or providing performance enhancement using the method of concurrently providing a left-side light stimulus to a left eye of the user, a right-side light stimulus to a right eye of the user, a left-side auditory stimulus to a left side of the user, and a right-side auditory stimulus to a right side of the user for a first time interval; alternating providing the left-side light stimulus and left-side auditory stimulus with providing the right-side light stimulus and right-side auditory stimulus for a second time interval; alternating providing the left-side and right-side light stimuli with providing the left-side and right-side auditory stimuli for a third time interval; and alternating providing the left-side light stimulus and right-side auditory stimulus with providing the right-side light stimulus and left-side auditory stimulus for a fourth time interval.

It is another aspect to provide a method of providing stimulation to a user, The method includes: providing a headset to be worn by the user; applying, with the headset, a left auditory stimulus pattern to the left side of a head of the user; and applying, with the headset, a right auditory stimulus pattern to the right side of the head, The applications of the left auditory stimulus pattern and the right auditory stimulus pattern are coordinated with one another.

These features together with the various ancillary provisions and features which will become apparent to those skilled in the art from the following detailed description, are attained by the methods and system for providing stimulation to a user of the present invention, embodiments thereof being shown with reference to the accompanying drawings, by way of example only, wherein:

DETAILED DESCRIPTION OF THE INVENTION

Figure 1A:
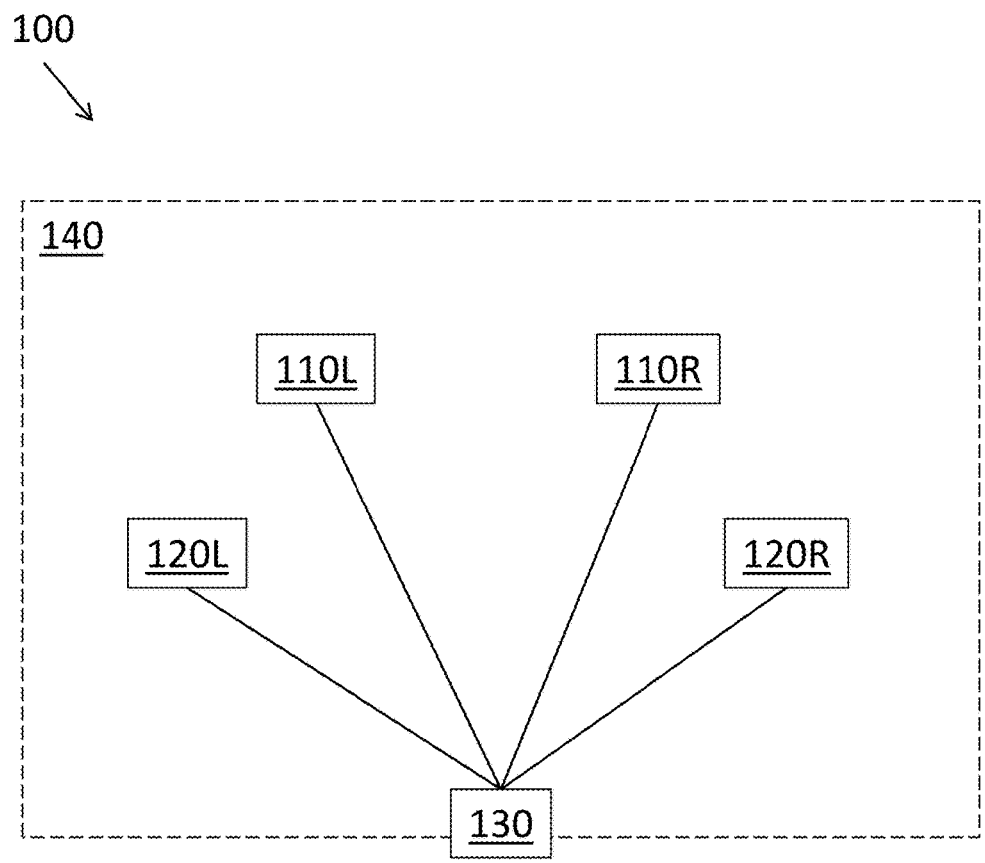
FIGS. 1A and 1B show schematic diagrams of therapeutic systems to provide therapeutic auditory, visual, and/or tactile stimulus, according to many embodiments of the present disclosure.

FIG. 1A is a schematic diagram of a first embodiment therapeutic system 100. Therapeutic system 100 provides one or more outputs that a person wearing the therapeutic system may experience as auditory, visual, and/or tactile stimulus. Thus, in one embodiment, therapeutic system may comprise a left light source 110L, a right light source 110R, a left vibration source 120L, a right vibration source 120R, and a controller 130 for independently controlling and coordinating the action of the light and vibration sources. Thus, for example, therapeutic system 100 may be positioned on the head of a user with left light source 110L positioned over the left eye to provide a left visual stimuli, right light source 110R positioned over the right eye to provide a right visual stimuli, left vibration source 120L positioned to provide left ear auditory stimuli, and right vibration source 120R positioned to provide right ear auditory stimuli.

In one embodiment, left and right light sources 110L, 110R may each comprise light-emitting diodes, an incandescent light source having a wavelength filter, a fluorescent light source, a backlit LCD panel, or other light source configured to provide to the user light at a desired, predetermined wavelength or wavelength range.

In another embodiment, left and right vibration sources 120L, 120R may each comprise earbuds, miniature speakers, or other vibration sources that can provide auditory stimuli to a user. In certain other embodiments, left and right vibration sources 120L, 120R may comprise bone conduction transducers in the audible frequency range to provide vibrations to the user's skull bone that is sensed as auditory by the user's ear. Optionally, one or more of left and right vibration sources 120L, 120R may also produce vibrations that are sensed as tactile stimuli. Thus, for example, controller 130 may provide first signals to bone conduction transducers that vibrate or oscillate at a first frequency that can be interpreted by the user as auditory stimuli and may provide second signals at a second, lower frequency that can be interpreted as a tactile sensation by the user. In other words, bone conduction transducers may be adapted to provide both auditory and tactile stimulus to the user.

In certain embodiments, left and right vibration sources 120L, 120R provide output at specific one or more frequencies or a range of frequencies, and are turned on and off at a stimulation frequency. Thus, for example, a vibration source may be programmed to provide an output at an audio frequency of 256 Hz for some period of time, followed by no output for the following period of time. Thus, the vibration source is the product of an audio frequency and a square wave.

Figure 1B:
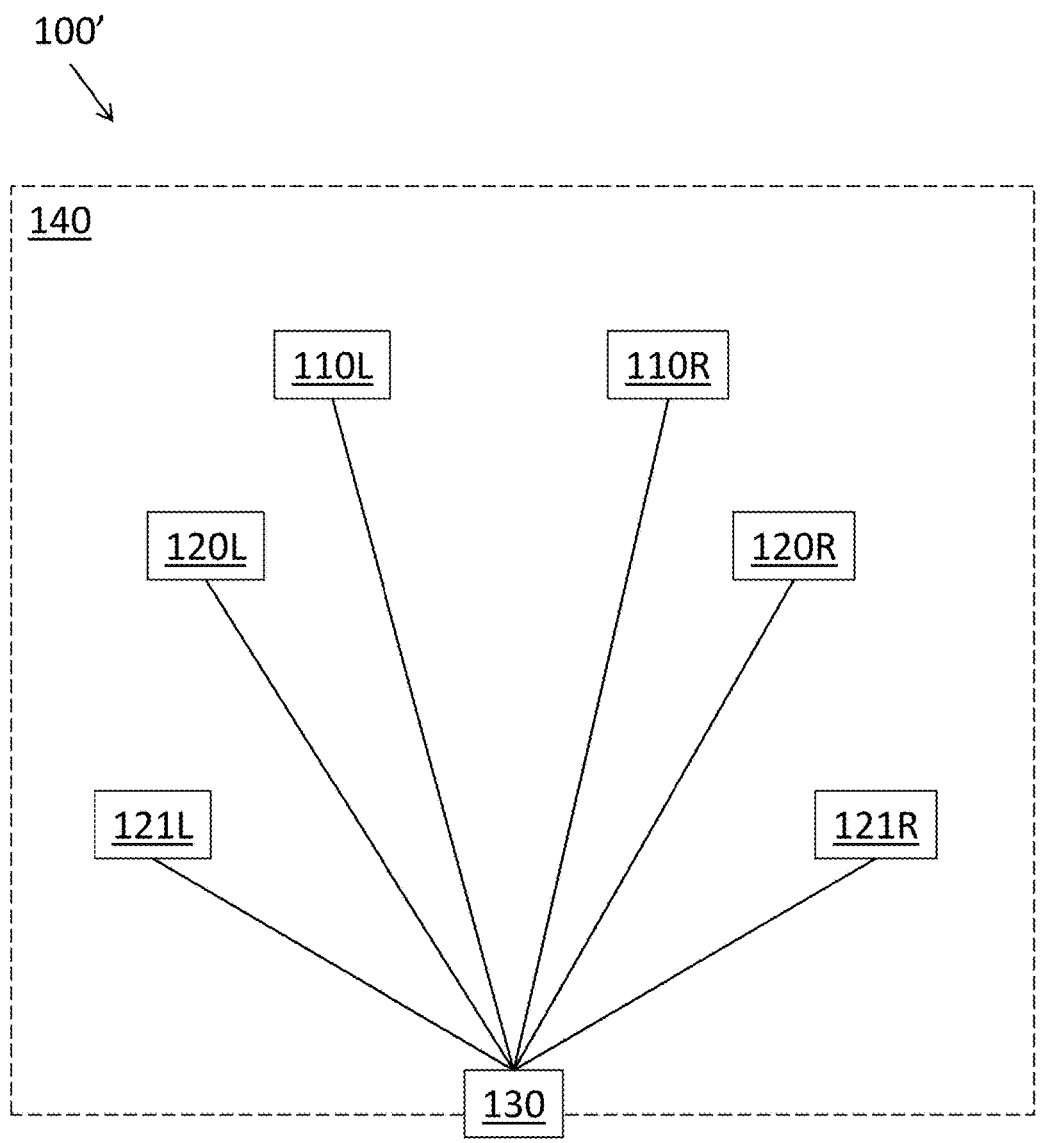

FIG. 1B is a schematic diagram of a second embodiment therapeutic system 100'. Second embodiment therapeutic system 100' is generally similar to first embodiment therapeutic system 100', except as explicitly noted. Specifically, second embodiment therapeutic system 100' includes a left tactile stimulus source 121L and a right tactile stimulus source 121R, each of which may be individually controlled and coordinated with the controller 130 to provide tactile stimuli to a user of therapeutic system 100'.

Figure 2A:
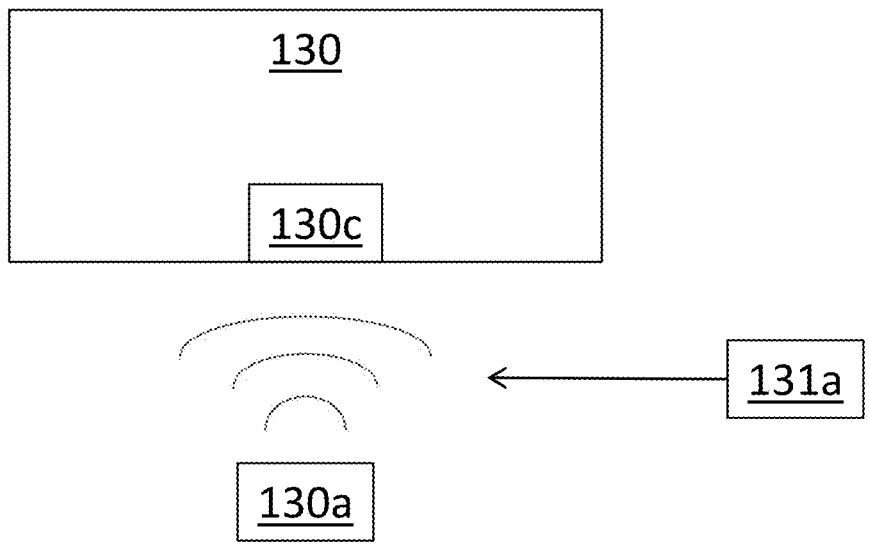
FIGS. 2A and 2B show schematic diagrams of the controller for the therapeutic systems of FIGS. 1A and 1B.
Figure 2B:
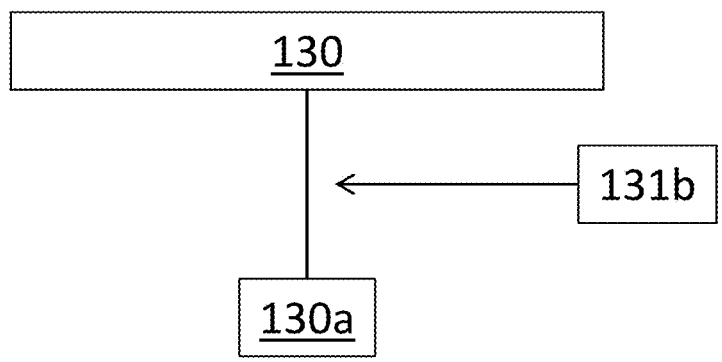

FIGS. 2A and 2B show schematic diagrams of the controller 130 of therapeutic system 100 or 100'. As shown in FIG. 2A, therapeutic system 100 or 100' may optionally include an external control unit 130a that may wirelessly communicate with a wireless receiver/transmitter 130c of the controller 130 through a wireless connection 131a. The wireless connection 431a may comprise a Bluetooth connection, a Bluetooth LE connection, a WiFi connection, a ZigBee connection, an infrared (IR) connection, a radiofrequency (RF) connection, or an inaudible auditory signal connection, to name a few examples. The external control unit 130a may comprise a custom-built, electronic controller. In many embodiments, the external control unit 130a may comprise a personal computing device of the user that may have downloaded onto and operating, a custom computer application or "app" to operate the system 100 or 100' to provide a therapeutic regimen. For example, the personal computing device may comprise a personal computer, a personal laptop computer, a tablet computer, or a smartphone. The custom computer application or "app" may be an application or "app" downloadable from an application distribution platform. The application may include one or more therapeutic regimens that the user may select for implementation by the therapeutic system 100 or 100'. In some embodiments, the application may allow the user to provide feedback information about the efficacy of the therapeutic regimen(s), the feedback may be uploaded and collected by a central server(s) in communication with the application, and the therapeutic regimen(s) may be improved or optimized based on the feedback from the one or more users. Alternatively or in combination, as shown in FIG. 2B, the system 100 or 100' may further comprise an external control unit 130a, such as a custom-built controller, that may communicate with the controller 130 through a wired connection 131a, for example, a USB, FireWire, or Lightning connection, to name a few examples.

Figure 3A:
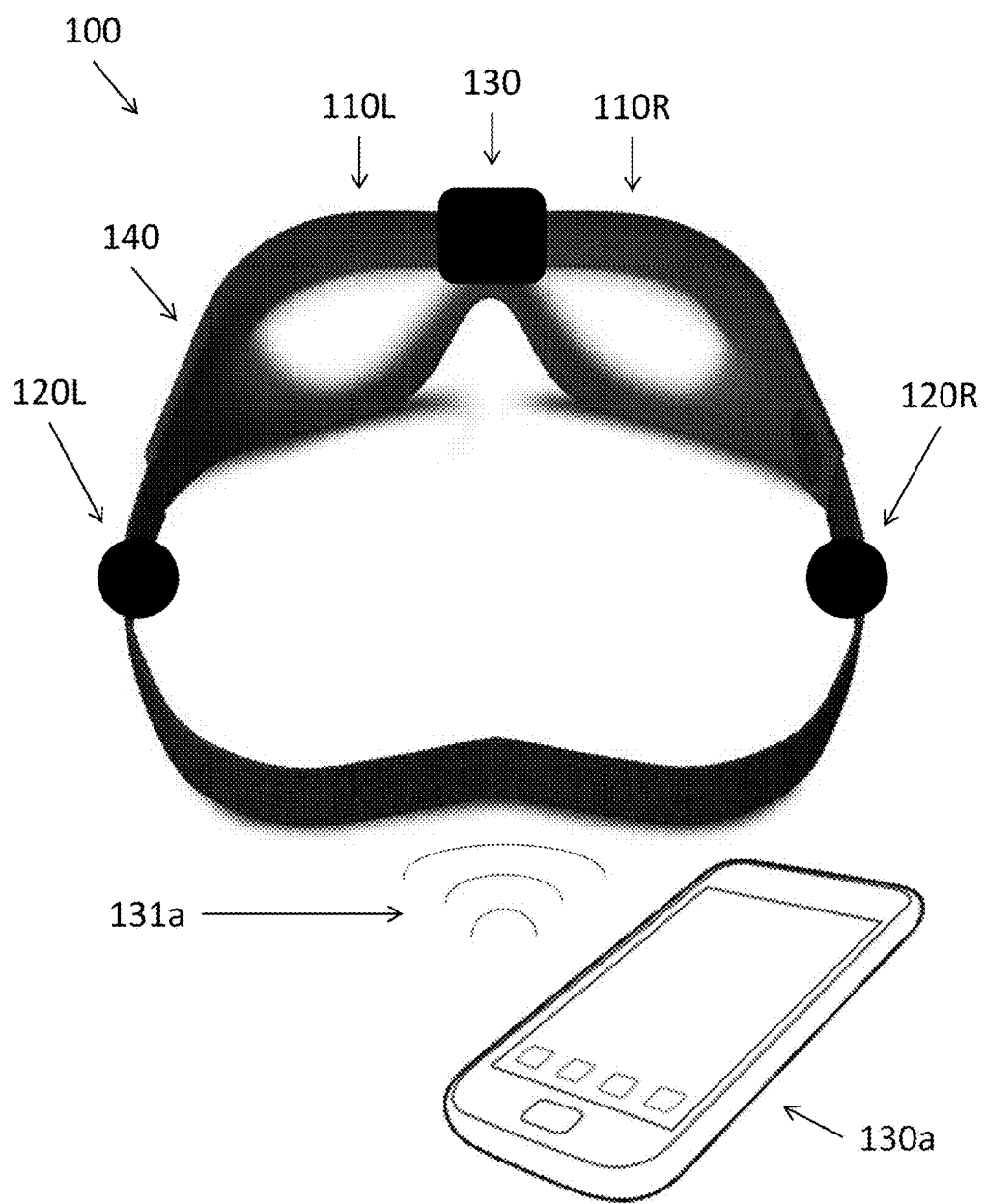
FIG. 3A shows an exemplary therapeutic wearable headset or sleep mask, according to many embodiments.

FIG. 3A shows one embodiment of the therapeutic system 100 as including therapeutic wearable headset or sleep mask 140 which integrates the light, vibration, and, optionally, tactile sources into a single form factor for presentation to a user. Thus, for example, when a user places wearable headset or sleep mask 140 on their head, left light source 110L is positioned over the left eye to provide a left visual stimuli, right light source 110R is positioned over the right eye to provide a right visual stimuli, left vibration source 120L is positioned to provide left ear auditory stimuli, and right vibration source 120R is positioned to provide right ear auditory stimuli.

As discussed above and herein, the left vibration source 120L and the right vibration source 120R may each comprise bone conduction transducer that may provide both auditory and tactile stimulus. Alternatively, wearable headset or sleep mask 140 is therapeutic system 100' which includes left tactile stimulus source 121L and right tactile stimulus source 121R, each of which may be individually controlled and coordinated with the controller 130, as described above regarding FIG. 1B.

Figure 3B:
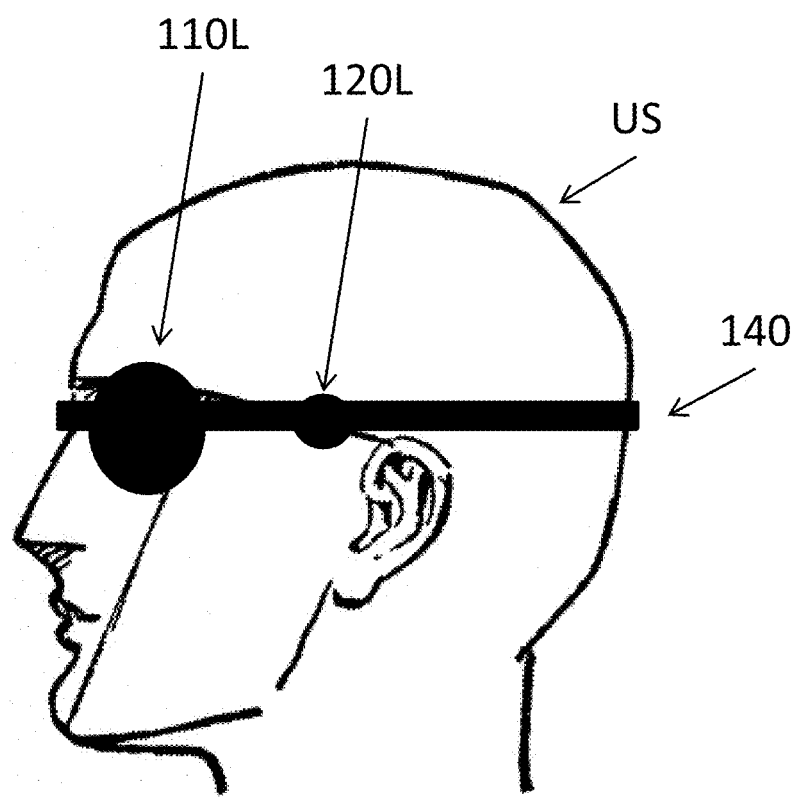
FIG. 3B shows a user wearing the therapeutic wearable headset and sleep mask of FIG. 3A.

As discussed above and herein, the therapeutic wearable headset or sleep mask 140 may be operated with an external controller 130a (e.g., a smartphone) in communication with the controller 130 through a wireless connection 131a, for example. The user US may have an option to turn tactile stimulation on or off, for example. FIG. 3B shows a user US wearing the therapeutic wearable headset or sleep mask 140.

Figure 4:
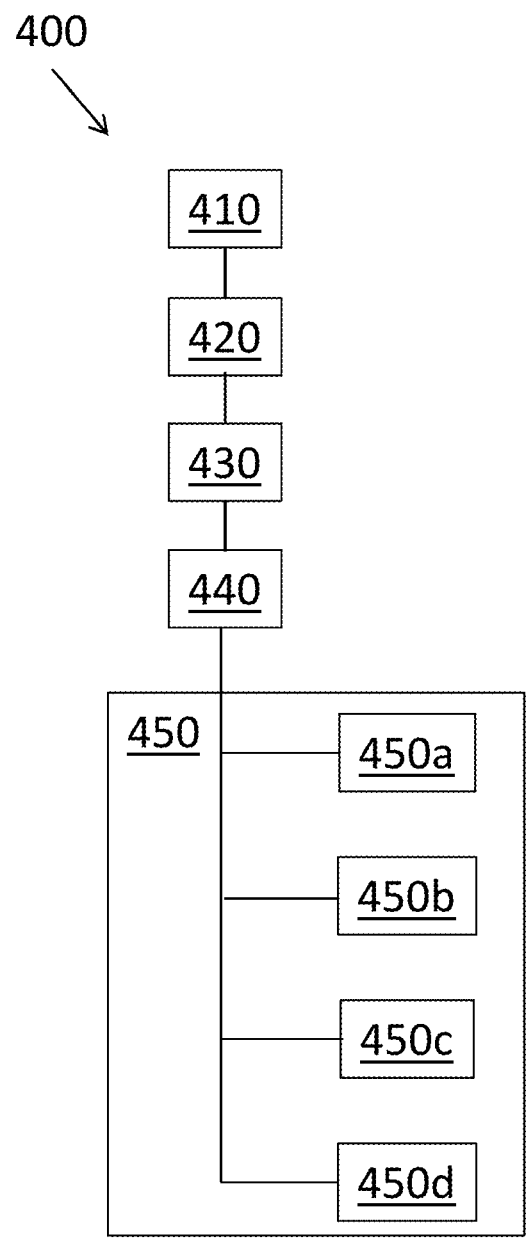
FIG. 4 shows a flow chart of a therapeutic method of providing therapeutic auditory, visual, and/or tactile stimulus, according to several embodiments.

FIG. 4 shows a flow chart of an exemplary therapeutic method 400 for providing therapeutic auditory, visual, and/or tactile stimulus. In a step 410, a subject having a neurological disorder or condition may be identified. Examples of neurological disorders may include, but are not limited to, insomnia, post-traumatic stress disorder (PTSD), brain injuries such as traumatic brain injury (TBI), mild traumatic brain injury (mTBI), or injuries to the brain due to oxygen deprivation, such as strokes, depression, anxiety, mood disorders, personality disorders, eating disorders, and psychotic disorders. Alternatively, a subject may be selected to undergo a therapeutic method 400 for the purpose of performance enhancement of mental and/or physical tasks for to aid the subject in napping or sleeping. In a step 420, the subject may be provided the therapeutic system or headwear, such as the system 100 or 100' described above. In a step 430, the subject may wear the therapeutic system or headwear, such as wearable headset or sleep mask 140. In a step 440, headset 140 executes programming 450 provided in controller 130 to provide stimuli to the subject. The programming provides two or more of auditory, video, and/or tactile stimulus are concurrently provided by headset 140 to the subject, and thus, for example, may provide power to activate left light source 110L, right light source 110R, left vibration source 120L and or right vibration source 120R.

As discussed above and herein, the left vibration source 120L and the right vibration source 120R may each comprise bone conduction transducer that may provide both auditory and tactile stimulus. Alternatively, wearable headset or sleep mask 140 is therapeutic system 100' which includes left tactile stimulus source 121L and right tactile stimulus source 121R, each of which may be individually controlled and coordinated with the controller 130, as described above regarding FIG. 1B.

In certain embodiments, providing two or more of auditory, video, and/or tactile stimulus concurrently may provide improved therapeutic benefits as compared to providing only one of auditory, video, or tactile stimulus at one time. The two or more auditory, video, and/or tactile stimulus may thus combine to provide the improved therapeutic benefits, for example (i.e., the two or more auditory, video, and/or tactile stimulus may synergize in a way to provide improved results over providing two of the stimuli individually.)

Exemplary instructions for providing stimuli may be provided, for example, by programming 450, such as a subroutine 450a, which includes the simultaneous activation of all active auditory, video, and/or tactile stimulus sources. Optionally, the activation of all sources may include the activation of tactile stimulation to run throughout all subsequent auditory and/or visual stimulation. Another exemplary subroutine 450b may comprise alternating the left auditory, video, and/or tactile stimulus sources with the right auditory, video, and/or tactile stimulus sources (i.e., the left stimuli and right stimuli take turns being active.) Another exemplary subroutine 450c may comprise alternating the visual sources with the auditory and/or tactile sources (i.e., the visual stimuli and the auditory/tactile stimuli take turns being active.) Another exemplary subroutine 450d may comprise alternating the left auditory and/or tactile source and the right visual source with the right auditory and/or tactile source and the left visual source (i.e., opposite auditory/tactile stimuli take turns being active.) Such programming is further described below.

In step 440, programming 450, including by not limited to subroutines 450a, 450b, 450c, and 450d, may each be applied one or more times, individually or in combination with one another. The programming may, in addition, provide sequences of output in subroutines 450a, 450b, 450c, and 450d at different frequencies and/or timings. Thus for example the subroutines may provide output at specific frequencies that change as the subroutine is repeated. Thus for example, subroutine 450a may provide auditory output to vibration source 120R or 120L at a frequency of 256 Hz that is turned on and off, that is it is pulsed, at a pulse frequency of 1 Hz for 2 minutes. This square pulse auditory signal thus generates signals at a frequency of 1 Hz in addition to higher harmonics. At a subsequent time the output at 256 Hz is pulsed at twice the previous pulse frequency for 2 minutes. In this manner, the auditory frequency of 256 Hz may be modulated over a wide range, including frequencies corresponding to brain wave frequencies.

In addition, by alerting the output between left and right channels, the brain may be stimulated in a way that it is forced to communicate between the left and right sides of the brain. This forced communication, for example, can allow PTSD memories to be wired to both sides of the brain, thereby stopping undesirable flashbacks.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, circuitry of the controller 130 or the external control unit 130a such as one or more of a processor or logic circuitry such as a central processing unit (CPU) or a programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

Example 1

The following describes an example of a stimulation pattern that has been found by empirical studies to be effective for inducing sleep, including napping, increasing neuroplasticity, treating brain injuries from strokes, TBI, or mTBI, improving balance, including improving fine motor control and reaction times, and treating PTSD, to name a few indications.

Light and auditory stimulus at a first frequency may be provided for a first time segment, then at a second lower frequency for a second time segment, and then at a third lower frequency for a third time segment. Each time segment may include one or more sub-segments of light and auditory stimulus, each sub-segment comprising one of the subroutines described above, for example. The light and auditory stimulus may end after a pre-determined time period, such as 20 minutes. The light and auditory stimulus may be ramped back up (i.e., starting from the third frequency, then transitioning to the second frequency, and finally transitioning to the third frequency), such as to wake the user. Alternatively or in combination, the light and auditory stimulus may be maintained at the second frequency such as to maintain a sleep state of the user. As described above, tactile stimulus may be provided concurrently with the auditory stimulus. The light may be provided at a wavelength of 580 nm and the auditory having a frequency of 256 Hz may be provided, or any of a number of auditory frequencies or combinations thereof that the subject can select as they wish.

Table 1 below describes an exemplary treatment regimen for this example. The stimulation provided in Table 1 first cycles through a block of four Segment A outputs, then cycles through a block of four Segment B outputs, then cycles through seven blocks of four Segment C outputs, and lastly repeats the block of four Segment A outputs. For Segment A outputs (A1, A2, A3, and A4), the auditory and light outputs cycle 115 or 116 times between being on for 0.1277 seconds and then being off for 0.1277 seconds (that is, at a pulse frequency of 3.9 Hz), followed by no output for 0.5 seconds. For Segment B outputs (B1, B2, B3 and B4), the auditory and light outputs cycle 44 or 45 times between being on for 0.3333 seconds and then being off for 0.3333 seconds (that is, at a pulse frequency of 1.5 Hz) followed by no output for 0.5 seconds. For Segment C outputs (C1, C2, C3 and C4), the auditory and light outputs cycle 14 or 15 times between being on for 1 second and then being off for 1 second (that is, a pulse frequency of 0.5 Hz), followed by no output for 1 second. Segments A1, B1, and C1 pulse the right and left sides of both the light and auditory together, with all outputs are synchronized to be on or off at the same time, as provided by subroutine 450a. Segments A2, B2, and C2 synchronize the left side light and auditory output, and the right side light and auditory output to be opposite to one another, as provided by subroutine 450b. Segments A3, B3, and C3 synchronize both lights together to be opposite to both auditory outputs, as provided by subroutine 450c. Segments A4, B4, and C4 synchronize the right auditory and light to be opposite to the left auditory and light outputs, as provided by subroutine 450d.

TABLE 1

| | Auditory Left | Auditory Right | Light Left | Light Right |
|---|---|---|---|---|
| Segments A1-A4 for 120 s | | | | |
| Segment A1 (Light and Auditory both sides pulse together) Repeat 116 times, followed by 0.5 sec gap | On 0.1277 s Off 0.1277 s | On 0.1277 s Off 0.1277 s | On 0.1277 s Off 0.1277 s | On 0.1277 s Off 0.1277 s |

TABLE 1-continued

| | Auditory Left | Auditory Right | Light Left | Light Right |
|---|---|---|---|---|
| Segment A2 (light and auditory on left side, alternating light and auditory on Right). Repeat 116 times, followed by 0.5 sec gap | On 0.1277 s Off 0.1277 s | Off 0.1277 s On 0.1277 s | On 0.1277 s Off 0.1277 s | Off 0.1277 s On 0.1277 s |
| Segment A3 (both lights together, alternating with both auditories together) Repeat 115 times, followed by 0.5 sec gap | On 0.1277 s Off 0.1277 s | On 0.1277 s Off 0.1277 s | Off 0.1277 s On 0.1277 s | Off 0.1277 s On 0.1277 s |
| Segment A4 (auditory left and light right together, alternating auditory right and light left together) Repeat 115 times, followed by 0.5 sec gap Segments B1-B4 for 120 s | On 0.1277 s Off 0.1277 s | Off 0.1277 s On 0.1277 s | Off 0.1277 s On 0.1277 s | On 0.1277 s Off 0.1277 s |
| Segment B1 (Light and Auditory both sides pulse together) Repeat 45 times, followed by 0.5 sec gap | On 0.3333 s Off 0.3333 s | On 0.3333 s Off 0.3333 s | On 0.3333 s Off 0.3333 s | On 0.3333 s Off 0.3333 s |
| Segment B2 (light and auditory on left side, alternating light and auditory on Right) Repeat 44 times, followed by 0.5 sec gap | On 0.3333 s Off 0.3333 s | Off 0.3333 s On 0.3333 s | On 0.3333 s Off 0.3333 s | Off 0.3333 s On 0.3333 s |
| Segment B3 (both lights together, alternating with both auditories together) Repeat 44 times, followed by 0.5 sec gap | On 0.3333 s Off 0.3333 s | On 0.3333 s Off 0.3333 s | Off 0.3333 s On 0.3333 s | Off 0.3333 s On 0.3333 s |
| Segment B4 (auditory left and light right together, alternating auditory right and light left together) Repeat 44 times, followed by 0.5 sec gap Repeat the following Segments C1-C4 7 times for a total of 14 minutes | On 0.3333 s Off 0.3333 s | Off 0.3333 s On 0.3333 s | Off 0.3333 s On 0.3333 s | On 0.3333 s Off 0.3333 s |
| Segment C1 (Light and Auditory both sides pulse together) Repeat 15 times, followed by 1 sec gap | On 1 sec Off 1 sec | On 1 sec Off 1 sec | On 1 sec Off 1 sec | On 1 sec Off 1 sec |
| Segment C2 (light and auditory on left side, alternating light and auditory on Right) Repeat 15 times, followed by 1 sec gap | On 1 sec Off 1 sec | Off 1 sec On 1 sec | On 1 sec Off 1 sec | Off 1 sec On 1 sec |
| Segment C3 (both lights together, alternating with both auditories together) Repeat 14 times, followed by 1 sec gap | On 1 sec Off 1 sec | On 1 sec Off 1 sec | Off 1 sec On 1 sec | Off 1 sec On 1 sec |
| Segment C4 (auditory left and light right together, alternating auditory right and light left together) Repeat 14 times, followed by 1 sec gap Segments A1-A4 for 120 s | On 1 sec Off 1 sec Off 1 sec | Off 1 sec On 1 sec On 1 sec | Off 1 sec On 1 sec On 1 sec | On 1 sec Off 1 sec Off 1 sec |
| Segment A1 (Light and Auditory both sides pulse together) Repeat 116 times, followed by 0.5 sec gap | On 0.1277 Off 0.1277 | On 0.1277 Off 0.1277 | On 0.1277 Off 0.1277 | On 0.1277 Off 0.1277 |
| Segment A2 (light and auditory on left side, alternating light and auditory on Right) Repeat 116 times, followed by 0.5 sec gap | On 0.1277 Off 0.1277 | Off 0.1277 On 0.1277 | On 0.1277 Off 0.1277 | Off 0.1277 On 0.1277 |
| Segment A3 (both lights together, alternating with both auditories together) | On 0.1277 Off 0.1277 | On 0.1277 Off 0.1277 | Off 0.1277 On 0.1277 | Off 0.1277 On 0.1277 |

TABLE 1-continued

|  | Auditory Left | Auditory Right | Light Left | Light Right |
|---|---|---|---|---|
| Repeat 115 times, followed by 0.5 sec gap |  |  |  |  |
| Segment A4 (auditory left and light right together, alternating auditory right and light left together) | On 0.1277<br>Off 0.1277 | Off 0.1277<br>On 0.1277 | Off 0.1277<br>On 0.1277 | On 0.1277<br>Off 0.1277 |
| Repeat 115 times, followed by 0.5 sec gap |  |  |  |  |

Example 2

The following describes an example of a stimulation pattern that has been found by empirical studies to be effective for inducing sleep. The stimulation pattern of Example 2 includes the part of the treatment regimen shown in Table 1. Specifically, the stimulation first cycles through a block of four Segment A outputs, then cycles through a block of four Segment B outputs, and then cycles through seven blocks of four Segment C outputs. The repetition of the last block of four Segment A outputs is not provided in Example 2.

Example 3

The following described example of a stimulation pattern that has been found by empirical studies to be effective for increasing alpha wave brain activity, inducing neuroplasticity, treating stroke or other brain injuries such as TBI, mTBI, including improving balance, improving fine motor control and reaction times, and treating PTSD, to name a few indications.

example. As described above, tactile stimulus may be provided concurrently with the auditory stimulus. The light may be provided at a wavelength of 580 nm and the auditory having a frequency of 432 Hz may be provided.

Table 2 below describes an exemplary treatment regimen for this example. The stimulation provided in Table 2 cycles through a block of four Segment A outputs 10 times. For Segment A1, A2, A3, and A4, the auditory and light outputs cycle 115 or 116 times between being on for 0.1277 seconds and then being off for 0.1277 seconds, followed by no output for 0.5 seconds. Segments A1 pulses the right and left sides of both the light and auditory together, with all outputs are synchronized to be on or off at the same time, as provided by subroutine 450a. Segment A2 synchronizes the left side light and auditory output, and the right side light and auditory output to be opposite to one another, as provided by subroutine 450b. Segment A3 synchronizes both lights together to be opposite to both auditory outputs, as provided by subroutine 450c. Segment A4 synchronizes the right auditory and light to be opposite to the left auditory and light outputs, as provided by subroutine 450d.

TABLE 2

|  | Auditory Left | Auditory Right | Light Left | Light Right |
|---|---|---|---|---|
| Repeat the following Segments A1-A4 10 times for a total time of 20 minutes |  |  |  |  |
| Segment A1 (Light and Auditory both sides pulse together)<br>Repeat 116 times, followed by 0.5 sec gap | On 0.1277 s<br>Off 0.1277 s | On 0.1277 s<br>Off 0.1277 s | On 0.1277 s<br>Off 0.1277 s | On 0.1277 s<br>Off 0.1277 s |
| Segment A2 (light and auditory on left side, alternating light and auditory on Right)<br>Repeat 116 times, followed by 0.5 sec gap | On 0.1277 s<br>Off 0.1277 s | Off 0.1277 s<br>On 0.1277 s | On 0.1277 s<br>Off 0.1277 s | Off 0.1277 s<br>On 0.1277 s |
| Segment A3 (both lights together, alternating with both auditories together)<br>Repeat 115 times, followed by 0.5 sec gap | On 0.1277 s<br>Off 0.1277 s | On 0.1277 s<br>Off 0.1277 s | Off 0.1277 s<br>On 0.1277 s | Off 0.1277 s<br>On 0.1277 s |
| Segment A4 (auditory left and light right together, alternating auditory right and light left together)<br>Repeat 115 times, followed by 0.5 sec gap | On 0.1277 s<br>Off 0.1277 s | Off 0.1277 s<br>On 0.1277 s | Off 0.1277 s<br>On 0.1277 s | On 0.1277 s<br>Off 0.1277 s |

In this example, the four subroutines described above and herein are applied and repeated for multiple time segments, each at a predetermined stimulation (repetition) frequency. The four subroutines may be repeated, such as with each segment of the four subroutines lasting 120 seconds, for Example 4

The following described yet another example of a stimulation pattern that has been found by empirical studies to be effective for increasing energy levels in the subject. Light and auditory stimulus at a first frequency may be provided for a first time segment, then at a second higher frequency for a second time segment, then back at the first frequency for a subsequent time segment, and so forth. Each time segment may include one or more sub-segments of light and auditory stimulus, each sub-segment comprising one of the subroutines described above, for example. The light and auditory stimulus may end after a pre-determined time period, such as 20 minutes. As described above, tactile stimulus may be provided concurrently with the auditory stimulus. The light may be provided at a wavelength of 580 nm and the auditory having a frequency of 432 Hz may be provided.

Table 3 below describes an exemplary treatment regimen for this example. The stimulation provided in Table 3 cycles ten times first through a block of four Segment A outputs, then through a block of four Segment D outputs. For Segment A outputs (A1, A2, A3, and A4), the auditory and light outputs cycle 115 or 116 times between being on for 0.1277 seconds and then being off for 0.1277 seconds, followed by no output for 0.5 seconds. For Segment D outputs (D1, D2, D3 and D4), the auditory and light outputs cycle 44 or 45 times between being on for 0.0667 seconds and then being off for 0.0667 seconds, followed by no output for 0.5 seconds. Segments A1 and D1 pulse the right and left sides of both the light and auditory together, with all outputs are synchronized to be on or off at the same time, as provided by subroutine 450*a*. Segments A2 and D2 synchronize the left side light and auditory output, and the right side light and auditory output to be opposite to one another, as provided by subroutine 450*b*. Segments A3 and D3 synchronize both lights together to be opposite to both auditory outputs, as provided by subroutine 450*c*. Segments A4 and D4 synchronize the right auditory and light to be opposite to the left auditory and light outputs, as provided by subroutine 450*d*.

TABLE 3

|  | Auditory Left | Auditory Right | Light Left | Light Right |
|---|---|---|---|---|
| Repeat 10 times: Segments A1-A4 followed by Segments D1-D4, for a total time of 20 minutes |  |  |  |  |
| Segment A1 (Light and Auditory both sides pulse together) Repeat 116 times, followed by 0.5 sec gap | On 0.1277 s Off 0.1277 s | On 0.1277 s Off 0.1277 s | On 0.1277 s Off 0.1277 s | On 0.1277 s Off 0.1277 s |
| Segment A2 (light and auditory on left side, alternating light and auditory on Right) Repeat 116 times, followed by 0.5 sec gap | On 0.1277 s Off 0.1277 s | Off 0.1277 s On 0.1277 s | On 0.1277 s Off 0.1277 s | Off 0.1277 s On 0.1277 s |
| Segment A3 (both lights together, alternating with both auditories together) Repeat 115 times, followed by 0.5 sec gap | On 0.1277 s Off 0.1277 s | On 0.1277 s Off 0.1277 s | Off 0.1277 s On 0.1277 s | Off 0.1277 s On 0.1277 s |
| Segment A4 (auditory left and light right together, alternating auditory right and light left together) Repeat 115 times, followed by 0.5 sec gap | On 0.1277 s Off 0.1277 s | Off 0.1277 s On 0.1277 s | Off 0.1277 s On 0.1277 s | On 0.1277 s Off 0.1277 s |
| Segment D1 (Light and Auditory both sides pulse together) Repeat 221 times, followed by 0.5 sec gap | On 0.0667 s Off 0.0667 s | On 0.0667 s Off 0.0667 s | On 0.0667 s Off 0.0667 s | On 0.0667 s Off 0.0667 s |
| Segment D2 (light and auditory on left side, alternating light and auditory on Right) Repeat 221 times, followed by 0.5 sec gap | On 0.0667 s Off 0.0667 s | Off 0.0667 s On 0.0667 s | On 0.0667 s Off 0.0667 s | Off 0.0667 s On 0.0667 s |
| Segment D3 (both lights together, alternating with both auditories together) Repeat 221 times, followed by 0.5 sec gap | On 0.0667 s Off 0.0667 s | On 0.0667 s Off 0.0667 s | Off 0.0667 s On 0.0667 s | Off 0.0667 s On 0.0667 s |
| Segment D4 (auditory left and light right together, alternating auditory right and light left together) Repeat 221 times, followed by 0.5 sec gap | On 0.0667 s Off 0.0667 s | Off 0.0667 s On 0.0667 s | Off 0.0667 s On 0.0667 s | On 0.0667 s Off 0.0667 s |

Example 5

The following Table 4 lists experimental results for the use of the inventive methods. The table lists what was being tested or treated, details of the conditions, the number of subjects, and the results of the tests. In each case, the stimulation in Example 1 for treating non-sleep related problems and for inducing a short sleep, and the stimulation in Example 2 was used for all other treatments.

Several of the treatments provided improvements in physical and/or mental performance, such as improving fine motor control and reaction times. This may be due to the device providing improved neuroplasticity in the days after treatment. Other treatments provided improvements in performing tasks and recovery from brain injury, such as injuries resulting from oxygen deprivation (strokes) and for those suffering from traumatic brain injury (TBI) or mild traumatic brain injury, and my provide improving balance, improving fine motor control. Other treatments provided relief to sufferers of PTSD by reducing the subject's response to triggering stimuli.

TABLE 4

| Treatment For | Details | No. of subjects | Results |
| --- | --- | --- | --- |
| Pain Management | Reduction of chronic nerve damage pain and improvement of sleep on self. Use of device for 3 months with 20 min/day of use of device | 1 | Eliminated chronic nerve damage pain for the time the device was used. |
| PTSD | Treating PTSD. Device use time of 5 hours. | 3 | Reduced flashbacks, nightmares and hypervigilance in all 3 subjects |
| Performance Enhancement | Marksmanship (rifles and pistols), endurance and speed driving (advanced surveillance, coordination and evasion). 6 hours training each subject. | 20 | Significant improvements in marksmanship in all participants and ease of concentration during speed driving, faster times on endurance trials for 19/20 subjects |
| Performance Enhancement | Fine motor skills on bomb disposal personnel 3 hours training with device | 3 | Improved performance of fine motor skills on bomb disposal VR simulation for all subjects |
| Performance Enhancement | Fine motor skills of surgeons - 3 hours training each | 3 | Improved performance of fine motor skills on surgical procedures VR simulation for all subjects. |
| Performance Enhancement | Pistol use and marksmanship. 3 hours training | 2 | 10% and 30% respectively increased speed in stripping and reassembling weapons. (average each of 5 tests, pre and post training) 6% average improvement in marksmanship scores - highly significant for such level of skill for all subjects |
| Performance Enhancement and PTSD | Performance by anti-terror and anti-drug squads of an elite firearms unit of a police force. 3 hours training each. | 5 | 10% average improvement in scores. Total absence of any PTSD |
| Performance Enhancement | Marksmanship. 2 hours training | 1 | average grouping shrunk from 5 inches to 1 inch at 200 yds. |
| Brain State | Increasing alpha activity. 4 hours total training time per subject. Group 1 L&S stimulation and biofeedback. Group 2 - just L&S stimulation Group 3 just biofeedback, Group 4 control. Double blinded - those administering had no idea of what was predicted to happen | 20 | Results as predicted. Group 1 greatest change, followed by group 2, Group 3 least change of active groups. Group 4 no change. |
| Performance Enhancement | Marksmanship | 3 + 15 | Significant improvement for all subjects. |
| Mental Performance Enhancement | Attention, learning and resistance to interrogation - 4 hours each person. Conduct after Capture course. | 3 | positive reports from all subjects |
| Performance Enhancement | Motion sickness for fixed wing aircraft pilots who have developed problems. 4 hours training per subject | 4 | Dramatic improvements in half of subjects. Small improvements in remaining half of subjects |
| PTSD | PTSD symptoms - test to remove neurological symptoms of flashbacks, nightmares and cold sweats | 33 | Successful in 31/33 subjects |
| Performance Enhancement | Driver performance using VR simulators for reaction speeds and performance under stress | 2 | Immediate increase in reaction speeds and improved performance for all subjects |
| Performance Enhancement | Professional soccer player performance. Trained for 4 hours. Battery of 21 tests | 1 | 5-25% increase in speeds to complete tests |
| Inducing Sleep | Sleep patterning and circadian rhythm adjustment for crews setting endurance records. members each year. Also used for improving safety drills when parachuting | 6 | All subjects fell asleep using the device during training, including one subject that was ill with a virus and couldn't otherwise sleep. |

TABLE 4-continued

| Treatment For | Details | No. of subjects | Results |
|---|---|---|---|
| Performance Enhancement | Race car driver performance. Ten days of training for 30 minutes per day. | 1 | Subject won his first Grand Prix of the season. |
| Performance Enhancement | Soccer player kicking performance. 5 days of 1 hour each day | 1 | Subject went from 5th ranked to highest ranked |
| Stroke Recovery | Use on 6 year post stroke subjects. four hours training. | 10 | Observable balance improvement in 7/10 subjects. 3 subjects had had dramatic improvements in their sleep. |
| Epilepsy Seizure Reduction | Effect on seizures of photosensitive epileptics. 4 hours training | 3 | One subject was found to not be epileptic. The other two subjects had a reduction in both severity and frequency of seizures, for at least a period of at least one month. |
| Concussion Recovery | Effect on concussions | 18 | All subjects appeared to have recovery happen at very fast speed. |
| Performance Enhancement | Effect on musical ability of a jazz musician. | 1 | Greatly improved performance speed |
| PTSD | PTSD. Treatment protocol lasting 3 sessions of 2 hours each | 22 | 19 individuals saw a cessation of major symptoms - flashbacks, nightmares, cold sweats and hypervigilance. the remaining 3 appeared to be calmer after treatment, but did not stop the major neurological symptoms |
| Sleep | Insomnia | 1 | Goes to sleep 4 times in 45 mins |
| Pain Management | Chronic Regional Pain Syndrome | 1 | Subject had constant pain on touching arms with no relief in 3 years Subject saw immediate pain relief on first use of the device. Continued use over the following weeks results in periods of time without pain grow up to four hours following each use. Averaging at two hours. |
| Pain Management and Sleep | Chronic pain | 1 | After six months of use, the subject continues getting 30% more sleep, and a significant reduction in pain. Device continues to be used 3-4 times a week for 20 min. |

Example Embodiments

The following are example embodiments.

An example embodiment 1 comprises a method of providing stimulation to a user, the method comprises: providing a headset to be worn by the user; applying, with the headset, a left visual stimulus pattern to the left eye of the user; applying, with the headset, a right visual stimulus pattern to the right eye of the user; applying, with the headset, a left auditory stimulus pattern to the left side of a head of the user; and applying, with the headset, a right auditory stimulus pattern to the right side of the head, wherein the applications of the left visual stimulus pattern, the right visual stimulus pattern, the left auditory stimulus pattern, and the right auditory stimulus pattern are coordinated with one another.

An example embodiment 2 including example embodiment 1, wherein applying, with the headset, the left auditory stimulus pattern comprises applying, with the headset, a left tactile stimulus pattern, and wherein applying, with the headset, the right auditory stimulus pattern comprises applying, with the headset, a right tactile stimulus pattern.

An example embodiment 3 including example embodiment 2, wherein the left tactile stimulus pattern and the right tactile stimulus pattern are configured to produce a plurality of concurrent left and right tactile signals.

An example embodiment 4 including example embodiment 2, wherein the left tactile stimulus pattern and the right tactile stimulus pattern are configured to produce a plurality of alternating left and right tactile signals.

An example embodiment 5 including example embodiment 2, wherein the left tactile stimulus pattern is coordinated with the left auditory stimulus pattern, and wherein the right tactile stimulus pattern is coordinated with the right auditory stimulus pattern.

An example embodiment 6 including example embodiment 5, wherein the left tactile stimulus pattern comprises a left-side vibration at a first frequency generated concurrently with auditory during the left auditory stimulus pattern, and wherein the right tactile stimulus pattern comprises a right-side vibration at a second frequency generated concurrently with auditory during the right auditory stimulus pattern.

An example embodiment 7 including example embodiment 6, wherein one or more of the left-side or right-side vibration is a vibration of from 0.5 Hz to 1.5 Hz.

An example embodiment 8 including any one of example embodiments 1 through 7, wherein applying, with the headset, the left auditory stimulus pattern comprises generating the left tactile stimulus pattern with a left bone conduction transducer of the headset, and wherein applying, with the headset, the right auditory stimulus pattern comprises generating the left tactile stimulus pattern with a left bone conduction transducer of the headset.

An example embodiment 9 including any one of example embodiments 1 through 7, wherein the left visual stimulus pattern and the right visual stimulus pattern are configured to produce a plurality of concurrent left and right light signals.

An example embodiment 10 including any one of example embodiments 1 through 7, wherein the left visual stimulus pattern and the right visual stimulus pattern are configured to produce a plurality of alternating left and right light signals.

An example embodiment 11 including any one of example embodiments 1 through 7, wherein the left auditory stimulus pattern and the right auditory stimulus pattern are configured to produce a plurality of concurrent left and right auditory signals.

An example embodiment 12 including any one of example embodiments 1 through 7, wherein the left auditory stimulus pattern and the right auditory stimulus pattern are configured to produce a plurality of alternating left and right auditory signals.

An example embodiment 13 including any one of example embodiments 1 through 12, wherein one or more of the left or right visual stimulus pattern has a light wavelength of from 550 nm to 610 nm.

An example embodiment 14 including any one of example embodiments 1 through 13, wherein one or more of the left or right visual stimulus pattern has a light wavelength of 580 nm.

An example embodiment 15 including any one of example embodiments 1 through 14, wherein one or more of the left or right auditory stimulus pattern includes an auditory frequency of from 240 Hz to 480 Hz.

An example embodiment 16 including any one of example embodiments 1 through 15, wherein one or more of the left or right auditory stimulus pattern includes an auditory frequency of 256 Hz or 432 Hz.

An example embodiment 17 including any one of example embodiments 1 through 16, wherein one or more of the left visual stimulus pattern comprises repeatedly pulsing a light at one or more of a first frequency, a second frequency less than the first frequency, or a third frequency less than the first and second frequencies.

An example embodiment 18 including any one of example embodiments 1 through 17, wherein the first frequency is between 3.75 Hz and 4.25 Hz, the second frequency is between 1.25 Hz and 1.75 Hz, and the third frequency is between 0.25 Hz and 0.75 Hz.

An example embodiment 19 including example embodiment 19, wherein the first frequency is 3.9 Hz, the second frequency is 1.5 Hz, and the third frequency is 1 Hz.

An example embodiment 20 including any one of example embodiments 18 and 19, wherein repeatedly pulsing the light comprises pulsing the light for a predetermined time interval.

An example embodiment 21 including example embodiment 20, wherein the predetermined time interval is 25-35 seconds.

An example embodiment 22 including any one of example embodiments 20 and 21, wherein the predetermined time interval is 30 seconds.

An example embodiment 23 including any one of example embodiments 1 through 22, wherein one or more of the left or right auditory stimulus pattern comprises a sequence stimulus patterns each having a pulse frequency having a pulse period, said repeating temporal signals including a portion of the pulse period with including an auditory frequency of from 240 Hz to 480 Hz and a portion of the pulse period.

An example embodiment 24 including example embodiment 23, wherein said portion of said pulse period is one half of the pulse period.

An example embodiment 25 including any one of example embodiments 23 and 24, wherein said sequence of stimulus patterns includes a first stimulus pattern having a first pulse frequency, a second stimulus pattern having a second pulse frequency less than the first pulse frequency, and a third stimulus pattern having a third pulse frequency less than the second pulse frequency.

An example embodiment 26 including example embodiment 25, wherein the first pulse frequency is between 3.75 Hz and 4.25 Hz, the second pulse frequency is between 1.25 Hz and 1.75 Hz, and the third pulse frequency is between 0.25 Hz and 0.75 Hz.

An example embodiment 27 including example embodiment 25 wherein the first pulse frequency is 3.9 Hz, the second pulse frequency is 1.5 Hz, and the third pulse frequency is 1 Hz.

An example embodiment 28 including any one of example embodiments 25 through 27, wherein said first stimulus pattern, said second stimulus pattern, or said third stimulus pattern stimulates for a predetermined time interval.

An example embodiment 29 including example embodiments 28, wherein the predetermined time interval is 25-35 seconds.

An example embodiment 30 including any one of example embodiments 28 and 29, wherein the predetermined time interval is 30 seconds.

An example embodiment 31 including any one of example embodiments 1 through 30, wherein the headset is in operative communication with an external control device.

An example embodiment 32 comprises a method of treating a neurological disease or condition or providing performance enhancement using the method of example embodiment 1.

An example embodiment 33 including example embodiment 32, where said neurological disease or condition comprises insomnia, post-traumatic stress disorder (PTSD), stokes or other brain injuries such as traumatic brain injury (TBI), or mild traumatic brain injury (mTBI).

An example embodiment 34 including example embodiment 32, where said performance enhancement is providing sleep, the improvement of mental capabilities, or the improvement of physical capabilities.

An example embodiment 35 including an apparatus to provide stimulation to a user, the apparatus comprises: a frame configured to be worn on a head of the user; a left light source configured to generate a left visual stimulus pattern; a right light source configured to generate a right visual stimulus pattern; a left auditory source configured to generate a left auditory stimulus pattern; a right auditory source configured to generate a right auditory stimulus pattern; and a controller coupled to the left light source, the right light source, the left auditory source, and the right auditory source, wherein applications of the left visual stimulus pattern, the right visual stimulus pattern, the left auditory stimulus pattern, and the right auditory stimulus pattern are independently controlled from one another but coordinated with one another by the controller.

An example embodiment 36 including example embodiment 35, wherein the left auditory source is further configured to generate a left tactile stimulus pattern, and wherein the right auditory source is further configured to generate a right tactile stimulus pattern.

An example embodiment 37 including any one of example embodiments 35 and 36, wherein one or more of the left or right auditory source comprises a bone conduction transducer.

An example embodiment 38 including any one of example embodiments 35 through 37, wherein the controller is configured to be in communication with and operated by an external control unit.

An example embodiment 39 including example embodiment 38, wherein the external control unit is in wireless communication with the controller.

An example embodiment 40, including any one of example embodiments 38 and 39, wherein the external control unit comprises one or more of a personal computer, a laptop computer, a tablet computer, a smartphone, or a wearable computer.

An example embodiment 41 including any one of example embodiments 38 through 40, wherein the external control unit has operating thereon an application configured to interface with and operate the controller.

An example embodiment 42 including any one of example embodiments 35 through 41, wherein one or more of the left or right light source comprises a light-emitting diode (LED).

An example embodiment 43 including any one of example embodiments 35 through 42, wherein one or more of the left or right light source is configured to generate light at 550-610 nm.

An example embodiment 44 including any one of example embodiments 35 through 42, wherein one or more of the left or right light source is configured to generate light at 580 nm.

An example embodiment 45 comprises a method to provide stimulation to a user, the method comprises: concurrently providing a left-side light stimulus to a left eye of the user, a right-side light stimulus to a right eye of the user, a left-side auditory stimulus to a left side of the user, and a right-side auditory stimulus to a right side of the user for a first time interval; alternating providing the left-side light stimulus and left-side auditory stimulus with providing the right-side light stimulus and right-side auditory stimulus for a second time interval; alternating providing the left-side and right-side light stimuli with providing the left-side and right-side auditory stimuli for a third time interval; and alternating providing the left-side light stimulus and right-side auditory stimulus with providing the right-side light stimulus and left-side auditory stimulus for a fourth time interval.

An example embodiment 46 including example embodiment 45, wherein the second time interval is after the first time interval, the third time interval is after the second time interval, and the fourth time interval is after the third time interval.

An example embodiment 47 including of any one of example embodiments 45 and 46, wherein one or more of the left-side or right-side light stimuli comprises pulsing a light at a predetermined pulsing frequency for one or more of the first, second, third, or fourth time intervals.

An example embodiment 48 including any one of example embodiments 45 through 47, wherein one or more of the left-side or right-side auditory stimuli comprises generating a auditory at a predetermined generation frequency for one or more of the first, second, third, or fourth time intervals.

An example embodiment 49 including any one of example embodiments 45 through 48, wherein the left-side light stimulus, the right-side light stimulus, the left-side auditory stimulus, and the right-side auditory stimulus are generated with a wearable headset.

An example embodiment 50 including any one of example embodiments 45 through 49, further comprises providing a left-side tactile stimulus concurrently with the left-side auditory stimulus and providing a right-side tactile stimulus concurrently with the right-side auditory stimulus.

An example embodiment 51 comprises a method of treating a neurological disease or condition or providing performance enhancement using the method of example embodiment 45.

An example embodiment 52 including example embodiment 51, where said neurological disease or condition comprises insomnia, post-traumatic stress disorder (PTSD), stokes or other brain injuries such as traumatic brain injury (TBI), or mild traumatic brain injury (mTBI).

An example embodiment 53 including example embodiment 51, where said performance enhancement is providing sleep, improving alpha wave activity, the improvement of mental capabilities, or the improvement of physical capabilities.

An example embodiment 54 comprises a method to provide stimulation to a user, the method comprises: providing a headset to be worn by the user; applying, with the headset, a left auditory stimulus pattern to the left side of a head of the user; and applying, with the headset, a right auditory stimulus pattern to the right side of the head, wherein the applications of the left auditory stimulus pattern and the right auditory stimulus pattern are coordinated with one another.

An example embodiment 55 including example embodiment 54, wherein the left auditory stimulus pattern and the right auditory stimulus pattern are configured to produce a plurality of concurrent left and right auditory signals.

An example embodiment 56 including example embodiment 54, wherein the left auditory stimulus pattern and the right auditory stimulus pattern are configured to produce a plurality of alternating left and right auditory signals.

An example embodiment 57 including any one of example embodiments 54 through 56, wherein one or more of the left or right auditory stimulus pattern includes an auditory frequency of from 240 Hz to 480 Hz.

An example embodiment 58 including any one of example embodiments 54 through 57, wherein one or more of the left or right auditory stimulus pattern includes an auditory frequency of 256 Hz or 432 Hz.

An example embodiment 59 including any one of example embodiments 54 through 58, wherein one or more of the left or right auditory stimulus pattern comprises a sequence stimulus patterns each having a pulse frequency having a pulse period, said repeating temporal signals including a portion of the pulse period with including an auditory frequency of from 240 Hz to 480 Hz and a portion of the pulse period.

An example embodiment 60 including example embodiment 59, wherein said portion of said pulse period is one half of the pulse period.

An example embodiment 61 including any one of example embodiments 59 and 60, wherein said sequence of stimulus patterns includes a first stimulus pattern having a first pulse frequency, a second stimulus pattern having a second pulse frequency less than the first pulse frequency, and a third stimulus pattern having a third pulse frequency less than the second pulse frequency.

An example embodiment 62 including example embodiment 61, wherein the first pulse frequency is between 3.75

Hz and 4.25 Hz, the second pulse frequency is between 1.25 Hz and 1.75 Hz, and the third pulse frequency is between 0.25 Hz and 0.75 Hz.

An example embodiment 63 including example embodiment 62, wherein the first pulse frequency is 3.9 Hz, the second pulse frequency is 1.5 Hz, and the third pulse frequency is 1 Hz.

An example embodiment 64 including any one of example embodiments 61 through 63, wherein said first stimulus pattern, said second stimulus pattern, or said third stimulus pattern stimulates for a predetermined time interval.

An example embodiment 65 including example embodiment 64, wherein the predetermined time interval is 25-35 seconds.

An example embodiment 66 including example embodiment 64, wherein the predetermined time interval is 30 seconds.

An example embodiment 67 including any one of example embodiments 54 through 66, wherein the headset is in operative communication with an external control device.

An example embodiment 68 comprises a method of treating a neurological disease or condition or providing performance enhancement using the method of example embodiment 54.

An example embodiment 69 including example embodiment 68, where said neurological disease or condition comprises insomnia, post-traumatic stress disorder (PTSD), or brain injuries such as traumatic brain injury (TBI), mild traumatic brain injury (mTBI), or strokes.

An example embodiment 70 including example embodiment 68, where said performance enhancement is providing sleep, the improvement of mental capabilities, or the improvement of physical capabilities.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of providing sensory stimulation to a user, the method comprising:
    alternating sensory stimulation between
    a first sensory stimulation including simultaneously providing a left visual stimulus pattern to a left eye of the user and a right auditory stimulus pattern to the right side of the head; and
    a second sensory stimulation including simultaneously providing a right visual stimulus pattern to a right eye of the user and a left auditory stimulus pattern to the left side of the head of the user,
    wherein one or more of the left auditory stimulus pattern or the right auditory stimulus pattern comprises a sequence of stimulus patterns including a first stimulus pattern having a first pulse frequency between 3.75 Hz and 4.25 Hz, a second stimulus pattern having a second pulse frequency between 1.25 Hz and 1.75 Hz, and a third stimulus pattern having a third pulse frequency between 0.25 Hz and 0.75 Hz.

2. The method of claim 1, further comprising:
    periodically providing a sensory stimulation including simultaneously providing a left visual stimulus pattern to the left eye of the user, a right visual stimulus pattern to the right eye of the user, a left auditory stimulus pattern to the left side of the head, and a right auditory stimulus pattern to the right side of the head of the user.

3. The method of claim 2, further comprising:
    alternating sensory stimulation between
    a third sensory stimulation including simultaneously providing a left visual stimulus pattern to the left eye of the user and a left auditory stimulus pattern to the left side of the head, and
    a fourth sensory stimulation including simultaneously providing a right visual stimulus pattern to the right eye of the user and a right auditory stimulus pattern to the right side of the head of the user.

4. The method of claim 3, further comprising:
    alternating sensory stimulation between
    a fifth sensory stimulation including simultaneously providing a left auditory stimulus pattern to the left side of the head and a right auditory stimulus pattern to the right side of the head, and
    a sixth sensory stimulation including simultaneously providing a left visual stimulus pattern to the left eye of the user and a right visual stimulus pattern to the right eye of the user.

5. The method of claim 1, wherein the left auditory stimulus pattern comprises generating the left auditory stimulus pattern with a left speaker, and wherein generating the right auditory stimulus pattern comprises generating the right auditory stimulus pattern with a right speaker.

6. The method of claim 1, wherein the left auditory stimulus pattern comprises generating the left auditory stimulus pattern with a left bone conduction transducer of a headset, and wherein the right auditory stimulus pattern comprises generating the left auditory stimulus pattern with a left bone conduction transducer of the headset.

7. The method of claim 1, wherein one or more of the left or right auditory stimulus pattern includes an auditory frequency of from 240 Hz to 480 Hz.

8. The method of claim 1, wherein one or more of the left visual stimulus pattern or right visual stimulus pattern comprises repeatedly pulsing a light at one or more of a first frequency, a second frequency less than the first frequency, or a third frequency less than the first and second frequencies.

9. The method of claim 8, wherein the first frequency is between 3.75 Hz and 4.25 Hz, the second frequency is between 1.25 Hz and 1.75 Hz, and the third frequency is between 0.25 Hz and 0.75 Hz.

10. The method of claim 9, wherein repeatedly pulsing the light comprises pulsing the light for a predetermined time interval.

11. The method of claim 10, wherein the predetermined time interval is 25-45 seconds.

12. The method of claim 1, wherein the sequence of stimulus patterns each have a pulse frequency having a pulse period, where a portion of the pulse period includes a stimulus of an auditory frequency of from 240 Hz to 480 Hz.

13. The method of claim 12, wherein said portion of said pulse period is one half of the pulse period.

14. The method of claim 1, wherein said first stimulus pattern, said second stimulus pattern, or said third stimulus pattern stimulates for a predetermined time interval.

15. The method of claim 14, wherein the predetermined time interval is 25-35 seconds.

16. The method of claim 15, wherein the predetermined time interval is 30 seconds.

17. A method of treating a neurological disease or condition or providing performance enhancement using the method of claim 1.

18. The method of claim 17, where said neurological disease or condition comprises insomnia, post-traumatic stress disorder (PTSD) or brain injury.

19. The method of claim 17, where said treating provides increased alpha wave activity in the brain.

20. The method of claim 19, where said performance enhancement is providing sleep, the improvement of mental capabilities, or the improvement of physical capabilities.

21. An apparatus to provide stimulation to a user, the apparatus comprising:
a frame configured to be worn on a head of the user;
a controller programmed to generate a plurality of inputs including a left light source input, a right light source input, a left auditory source input, and a right auditory source input;
a left light source configured to generate a left visual stimulus pattern from said left light source input;
a right light source configured to generate a right visual stimulus pattern from said right light source input;
a left auditory source configured to generate a left auditory stimulus pattern from said left auditory source input; and
a right auditory source configured to generate a right auditory stimulus pattern from said right auditory source input;
where said controller is programmed to generate inputs which alternate between
a first input including simultaneously generating the left light source input and the right auditory source input, and
a second input including simultaneously generating the right light source input and the left auditory source input,
wherein one or more of the left auditory source input or the right auditory source input comprises a sequence of stimulus patterns including a first stimulus pattern having a first pulse frequency between 3.75 Hz and 4.25 Hz, a second stimulus pattern having a second pulse frequency between 1.25 Hz and 1.75 Hz, and a third stimulus pattern having a third pulse frequency between 0.25 Hz and 0.75 Hz.

22. The apparatus of claim 21, wherein one or more of the left auditory source or the right auditory source is a speaker.

23. The apparatus of claim 21, wherein one or more of the left auditory source or the right auditory source is a bone conduction transducer.

24. The apparatus of claim 21, wherein one or more of the left or right light source comprises a light-emitting diode (LED).

25. The apparatus of claim 24, wherein one or more of the left or right light source is configured to generate light at 550-610 nm.

26. The apparatus of claim 24, wherein one or more of the left or right light source is configured to generate light at 580 nm.

27. A method of treating a neurological disease or condition or providing performance enhancement, said method comprising:
providing a headset to be worn by a user;
providing sensory stimulation to the user from the headset, where said stimulation alternates between
a first sensory stimulation including simultaneously providing a left visual stimulus pattern to a left eye of the user and a right auditory stimulus pattern to the right side of the head, and
a second sensory stimulation including simultaneously providing a right visual stimulus pattern to a right eye of the user and a left auditory stimulus pattern to the left side of the head of the user,
wherein one or more of the left auditory stimulus pattern or the right auditory stimulus pattern comprises a sequence of stimulus patterns including a first stimulus pattern having a first pulse frequency between 3.75 Hz and 4.25 Hz, a second stimulus pattern having a second pulse frequency between 1.25 Hz and 1.75 Hz, and a third stimulus pattern having a third pulse frequency between 0.25 Hz and 0.75 Hz.

28. The method of claim 27, where said neurological disease or condition comprises insomnia, post-traumatic stress disorder (PTSD) or brain injury.

29. The method of claim 27, where said treating provides increased alpha wave activity in the brain.

30. The method of claim 27, where said performance enhancement is providing sleep, the improvement of mental capabilities, or the improvement of physical capabilities.

* * * * *

UNITED STATES PATENT AND TRADEMARK OFFICE
CERTIFICATE OF CORRECTION

PATENT NO. : 10,328,236 B2  
APPLICATION NO. : 15/360808  
DATED : June 25, 2019  
INVENTOR(S) : Richard Hanbury Page 1 of 1

It is certified that error appears in the above-identified patent and that said Letters Patent is hereby corrected as shown below:

In the Claims

Column 24  
Claim 6, Line 37, "the left auditory" should be --the right auditory--

Column 24  
Claim 6, Line 38, "a left bone" should be --the right bone--

Signed and Sealed this  
Twenty-fifth Day of August, 2020

Andrei Iancu  
*Director of the United States Patent and Trademark Office*